United States Patent [19]

Cuzzato et al.

[11] Patent Number: 5,600,037
[45] Date of Patent: Feb. 4, 1997

[54] PROCESS FOR ISOMERIZING 1,1,2-TRIFLUORO-1,2-DICHLOROETHANE TO 1,1,1-TRIFLUORO-2,2-DICHLOROETHANE

[75] Inventors: Paolo Cuzzato, Treviso; Letanzio Bragante; Antonio Masiero, both of Padua, all of Italy

[73] Assignee: Ausimont S.p.A., Milan, Italy

[21] Appl. No.: 482,740

[22] Filed: Jun. 7, 1995

Related U.S. Application Data

[63] Continuation of Ser. No. 185,773, Jan. 24, 1994, abandoned, which is a continuation of Ser. No. 961,376, Oct. 15, 1992, abandoned.

[30] Foreign Application Priority Data

Oct. 18, 1991 [IT] Italy ................. MI91A2765

[51] Int. Cl.⁶ ............. C07C 17/00; C07C 19/08; C07C 17/38
[52] U.S. Cl. ............. 570/151; 570/163; 570/177
[58] Field of Search .............. 570/151, 163, 570/177

[56] References Cited

U.S. PATENT DOCUMENTS

| | | | |
|---|---|---|---|
| 4,766,260 | 8/1988 | Manzer | 510/188 |
| 4,925,993 | 5/1990 | Zawalski | 570/151 |

FOREIGN PATENT DOCUMENTS

| | | |
|---|---|---|
| 0282005A1 | 9/1988 | European Pat. Off. |
| 0317981 | 5/1989 | European Pat. Off. |
| 0376686A1 | 7/1990 | European Pat. Off. |
| 0450467A3 | 10/1991 | European Pat. Off. |
| 0450467A2 | 10/1991 | European Pat. Off. |
| 0121710 | 10/1978 | Japan ................. 510/151 |

OTHER PUBLICATIONS

Chemical Abstracts, vol. 112, No. 19, 7 May 1990, abstract No. 178054q, Shinsuke Morkiawa et al, "Isomerization of hydrogen–containing chlorofluorohydrocarbons", which is an English Abstract of Japanese Patent No. 01258630.

*Primary Examiner*—Alan Siegel
*Attorney, Agent, or Firm*—Bryan Cave LLP

[57] ABSTRACT

1,1,2-trifluoro-1,2-dichloroethane (A123a) is isomerized to 1,1,1-tri-fluoro-2,2-dichloroethane (A123) by contacting it with $AlF_3$ at temperatures ranging from 180° to 400° C. Advantageously, it is operated with mixtures of A123a with A123 and/or other chlorofluorocarbons coming from the preparation of A123 by hydrofluorination of perchloroethylene.

11 Claims, No Drawings

PROCESS FOR ISOMERIZING 1,1,2-TRIFLUORO-1,2-DICHLOROETHANE TO 1,1,1-TRIFLUORO-2,2-DICHLOROETHANE

This is a continuation of U.S. application Ser. No. 08/185,773, filed Jan. 24, 1994, now abandoned which is a continuation of U.S. application Ser. No. 07/961,376, filed Oct. 15, 1992, now abandoned.

The present invention generally relates to a process for isomerizing 1,1,2-trifluoro-1,2-dichloroethane (hereinafter referred to as A123a) to 1,1,1-trifluoro-2,2-dichloroethane (hereinafter referred to as A123). In particular it relates to the removal of A123a from its mixtures with A123 and optionally other chlorofluorocarbons by isomerizing A123a to A123.

The need for having available industrial processes for preparing A123 as free as possible from A123a has been recognized.

Such need is particularly recognized, for example, by the manufacturers of polyurethane foams, for the production of which A123 is used as foaming agent. In such case, the A123a contained therein decomposes and forms HCl, which corrodes the metal circuits of the plants.

The industrially most interesting processes for the preparation of A123 are based on the hydrofluorination of tetrachloroethylene in the gas phase, in the presence of proper catalysts.

Such a process is described for example in U.S. Pat. No. 4,766,260.

Such a preparation method always gives rise to A123a in amounts ranging from 5 to 20%, depending on the reaction conditions. Such product is difficult to be distilled-off from A123.

In principle it is possible to carry out the reaction under such conditions as to minimize the formation of A123a, for example by using high temperatures (about 360° C.); however, this is of little practical interest because under such conditions the process selectivity towards A123 is too low, while unacceptable amounts of by-products are obtained.

It is also possible to reduce the A123a content in the final reaction product by subjecting the mixture of A123 and A123a to a treatment with anhydrous HF in the presence of the same catalyst as is used for its preparation, thereby obtaining the preferential fluorination of A123a to 1,1,1,2-tetrafluoro-2-chloroethane (A124).

However, the selectivity of such reaction is not high enough, wherefore also the fluorination of considerable amounts of A123 occurs.

The Applicant has now surprisingly found a process—constituting the object of the present invention—for converting A123a to A123 by contacting A123a, either alone or in admixture with A123 and/or other chlorofluorocarbons, in the gas phase, with a catalyst consisting of aluminium trifluoride ($AlF_3$), at temperatures ranging from 180° to 400° C., but preferably from 220° to 320° C.

The aluminium trifluoride utilized herein as a catalyst is generally present in the crystallographic forms $\beta$, $\Delta$ and/or $\gamma$. However, little amounts of other crystalline forms are not harmful.

Said $AlF_3$ can be obtained by fluorination of alumina ($Al_2O_3$) with anhydrous HF or other fluorinating agents; or it can be prepared according to other methods of the art, such as, for example, the thermal decomposition of $Na_3AlF_6$.

In the case of the fluorination of $Al_2O_3$, the $AlF_3$ obtained has a surface area of 15–30 $m^2/g$ and granule sizes ranging from 20 to 200 microns (on the average: 80 microns).

The surface area of $AlF_3$ is not a critical element for the process of the invention, however, an $AlF_3$ having a high surface area, for example ranging from 15 to 30 $m^2/g$, is preferred.

If such $AlF_3$ is obtained by fluorination of $Al_2O_3$ with anhydrous HF it is preferable, although not absolutely necessary, if at least 90% of the alumina contained therein is present in the fluorinated state.

The $AlF_3$ utilized as a catalyst in the process of the invention can be modified, in order to increase the activity thereof, by addition of little amounts—not exceeding 1% by weight calculated on the catalyst—of transition metals, preferably Fe, Ni, Co, Mn.

Preferably, the process of the invention is utilized for the isomerization of A123a in its mixtures mainly with A123 and optionally with other chlorofluorocarbons, which are obtained in the processes for the fluorination of tetrachloroethylene with HF, in the gas phase.

In fact, the presence of products other than the isomers A123a and A123, for example A124 ($CF_3CHClF$), in the gaseous mixture obtained from such reaction does not prevent the isomerization of A123a. That is very advantageous in practice because it eliminates the necessity to carry out an accurate distillation of such products prior to the isomerization reaction. On the other hand, the fact that the reaction mixture directly flows into the isomerization reactor does not sensibly modify the content of the products different from said isomers and present in the reaction mixture, which can be then recovered as such or recycled to the A123 production.

For the purposes of the process of the invention, the contact times of A123a with the catalyst are not particularly critical. Generally they are maintained from 5 to 100 seconds and preferably from 20 to 50 seconds.

Also the pressure does not exhibit particularly critical values; it can be the atmospheric pressure or a higher pressure.

The following examples are given merely to illustrate the invention, but not to limit the scope thereof.

EXAMPLE 1

Into a tubular reactor made of Inconel 600® having an inside diameter of 5 cm and a length of 80 cm, equipped with a porous bottom of sintered Inconel 600 and heated by means of heating elements, there were introduced 300 cc (340 g) of $AlF_3$ having a specific surface of about 20 $m^2/g$. Such $AlF_3$ had been prepared by fluorination of $Al_2O_3$ with anhydrous HF till obtaining the fluorination of more than 90% of $Al_2O_3$.

The catalyst was treated with anhydrous HF at 250° C. for 2 hours in order to remove the moisture absorbed during the storing time.

About 100 g/h of a mixture containing 14.5 moles-% of A123a, 63.9 moles-% of A123 and 21.6 moles-% of other organic chlorofluorocarbons, mainly A124, were fed at a temperature of 240° C.

The gases leaving the reactor were bubbled in water in order to remove acidity traces, were dried and condensed in a cold trap and then analyzed by means of gas chromatography (G.C.).

The results obtained are reported in Table 1A.

After a 60–65 hour run, the catalyst exhibited exhaustion phenomena, but the activity (expressed as the A123a fraction isomerized to A123) could be restored by raising the temperature to 270° C. without affecting the selectivity, expressed as ratio between fed A123 (sum of the isomers) and recovered A123, as shown in Table 1B.

By raising the temperature further on (Table 1C) it was possible to maintain the activity as the catalyst got exhausted, the selectivity losses being only negligible.

Lastly, by regenerating the catalyst by means of a treatment with air at 430° C. followed by refluorination with anhydrous HF at 300° C., the original activity was fully restored (Table 1D).

EXAMPLE 2

Into the same reactor utilized in Example 1, 300 cc of $AlF_3$ having the same characteristics as the one of example 1 were charged.

The reagent mixture was fed without subjecting the catalyst to any preliminary hydrofluorination treatment. By operating in like manner as in example 1, the results reported in Table 2 were obtained.

EXAMPLE 3

Into the same reactor as Example 1 there were charged 310 cc of the same $AlF_3$, which was treated for 3 hours at 400° C. with air and then was fluorinated for 2 hours at 400° C. with anhydrous HF.

By operating as in example 1, the results reported in Table 3 were obtained.

EXAMPLE 4

Into the reactor of example 1 there were charged 310 cc of an aluminium fluoride containing 0.12% by weight of iron in the form of $Fe_2O_3$, which was treated for 2 hours at 300° C. with anhydrous HF.

By operating as in example 1, the results reported in Table 4 were obtained, wherefrom it is evident that the activity is much higher.

TABLE 1A

| | Feeding (Moles-%) | Operation hours | | | | | | | | |
|---|---|---|---|---|---|---|---|---|---|---|
| | | 1.5 | 4 | 13 | 21 | 24.5 | 29.5 | 40 | 57.5 | 66 | 80 |
| | | Obtained products (moles-%) | | | | | | | | |
| A123a | 14.5 | 4.2 | 2.3 | 5.2 | 4.5 | 4.3. | 4.0 | 5.0 | 4.4 | 9.8 | 10.2 |
| A123 | 63.9 | 75.8 | 75.6 | 73.3 | 74.4 | 74.9 | 75.0 | 74.1 | 75.0 | 69.1 | 68.8 |
| Others | 21.6 | 20.0 | 22.1 | 21.5 | 21.1 | 20.8 | 21.0 | 20.9 | 20.6 | 21.1 | 21.0 |

Reaction temperature = 240° C.;
t = 38"

TABLE 1B

| | Feeding (Moles-%) | Operation hours | | | | |
|---|---|---|---|---|---|---|
| | | 88 | 91.5 | 103.5 | 107 | 111 |
| | | Obtained products (moles-%) | | | | |
| A123a | 14.5 | 2.3 | 1.8 | 1.9 | 3.4 | 4.5 |
| A123 | 63.9 | 75.6 | 77.3 | 77.6 | 76.0 | 73.8 |
| Others | 21.6 | 22.1 | 20.9 | 20.5 | 20.6 | 21.7 |

Reaction temperature = 270° C.;
t = 36"

TABLE 1C

| | Feeding (moles-%) | Operation hours | | | | | | | | |
|---|---|---|---|---|---|---|---|---|---|---|
| | | 116 | 129 | 133 | 157 | 161 | 164 | 178 | 181 | 184 |
| | | Obtained products (moles-%) | | | | | | | | |
| A123a | 14.7 | 3.1 | 2.2 | 2.5 | 2.5 | 2.7 | 2.3 | 2.5 | 2.7 | 3.0 |
| A123 | 65.9 | 76.8 | 77.7 | 77.4 | 77.3 | 77.5 | 77.0 | 76.5 | 76.3 | 79.6 |
| Others | 19.4 | 20.1 | 20.1 | 20.1 | 20.2 | 19.8 | 20.7 | 21.0 | 21.0 | 19.4 |

Reaction temperature = 280° C.–320° C.;
(t = 36"–33", respectively)

TABLE 1D

| | Feeding (moles-%) | Operation hours | | | | |
|---|---|---|---|---|---|---|
| | | 4 | 7 | 11 | 24 | 26 |
| | | Obtained products (moles-%) | | | | |
| A123a | 10.6 | 0.3 | 0.2 | 0.2 | 5.0 | 2.3 |
| A123 | 65.4 | 72.1 | 72.8 | 74.2 | 73.1 | 75.6 |
| Others | 24.0 | 27.6 | 27.0 | 25.6 | 21.9 | 22.1 |

After regeneration -
Reaction temperature = 280° C. for tests not exceeding 11 operation hours, and 240° C. for tests not exceeding 26 operation hours
(t = 36" and 38", respectively)

TABLE 2

| Feeding (moles-%) | Operation hours | | | | | | | | | |
|---|---|---|---|---|---|---|---|---|---|---|
| | 3 | 7.5 | 11 | 14 | 18 | 23 | 26 | 30 | 33 | 38 |
| | Obtained products (moles-%) | | | | | | | | | |
| A123a  14.1 | 13.2 | 7.5 | 7.0 | 0.9 | 1.3 | 0.4 | 0.4 | 0.3 | 0.5 | 0.8 |
| A123   70.2 | 71.6 | 78.0 | 78.0 | 85.0 | 85.1 | 85.2 | 85.4 | 84.6 | 84.3 | 84.2 |
| Others 15.7 | 15.2 | 14.5 | 15.0 | 14.1 | 13.6 | 14.6 | 14.2 | 15.1 | 15.2 | 14.5 |

Reaction temperature = 240° C. for test not exceeding 11 operation hours;
t = 38"
Reaction temperature = 280° C. for the other tests;
t = 36"

TABLE 3

| Feeding (moles-%) | Operation hours | | | | |
|---|---|---|---|---|---|
| | 2 | 4.5 | 12 | 25 | 29 |
| | Obtained products (moles-%) | | | | |
| A123a  10.6 | 0.2 | 0.2 | 0.2 | 0.6 | 0.3 |
| A123   65.4 | 73.2 | 75.6 | 74.8 | 79.0 | 72.7 |
| Others 24.0 | 26.6 | 24.2 | 25.0 | 20.4 | 27.0 |

Reaction temperature = 280° C. for tests not exceeding 12 operation hours;
t = 37"
Reaction temperature = 260° C. for the other tests;
t = 38"

TABLE 4

| Feeding (moles-%) | Operation hours | | | | | |
|---|---|---|---|---|---|---|
| | 3.5 | 7.5 | 9 | 13.5 | 16.5 | 20 |
| | Obtained products (moles-%) | | | | | |
| A123a  14.1 | 0.6 | 0.1 | 0.6 | 0.6 | 0.3 | 1.4 |
| A123   70.2 | 69.6 | 57.4 | 76.1 | 75.3 | 77.4 | 77.2 |
| Others 15.7 | 29.2 | 42.5 | 23.7 | 24.1 | 22.3 | 21.4 |

Reaction temperature = 260° C. for tests not exceeding 7.5 operation hours;
t = 38"
Reaction temperature = 240° C. for tests not exceeding 13.5 operation hours;
t = 40"
Reaction temperature = 220° C. for the other two tests;
t = 41"

We claim:

1. A process for removing 1,1,2-trifluoro-1,2-dichloroethane (A123a) from a mixture comprising 1,1,1-trifluoro-2,2-dichloroethane (A123) and A123a, which comprises isomerizing A123a to A123 by contacting said mixture in the vapor phase with a catalyst consisting essentially of $AlF_3$ and transition metals selected from the group consisting of Fe, Mn, Co, and Ni, in an amount of from 0 to 1% by weight, at a temperature of from 200° C. to 400° C.

2. The process of claim 1, wherein said mixture further comprises 1,1,1-tetrafluoro-2-chloroethane (A124).

3. The process of claim 1, wherein said mixture is a reaction mixture obtained from hydrofluorination of perchloroethylene with HF.

4. The process of claim 1, wherein the temperature is within the range of from 220° to 320° C.

5. The process of claim 1, wherein the catalyst is prepared by fluorinating $Al_2O_3$ with anhydrous HF.

6. The process of claim 5, wherein at least 90% of the alumina in said catalyst is fluorinated.

7. A process for the production of 1,1,1-trifluoro-2,2-dichloroethane (A123) which comprises:
   (a) contacting tetrachloroethylene with HF to produce a mixture of hydrofluorination products, including 1,1,2-trifluoro-1,2-dichloroethane (A123a) and A123; and
   (b) isomerizing A123a to A123 by contacting said mixture in the vapor phase with a catalyst consisting essentially of $AlF_3$ and transition metals selected from the group consisting of Fe, Mn, Co, and Ni, in an amount of from 0 to 1% by weight, at a temperature of from 200° C. to 400° C.

8. The process of claim 7, wherein the mixture reacted in step (a) further comprises 1,1,1-tetrafluoro-2-chloroethane (A124).

9. The process of claim 7, wherein the temperature in step (b) is within the range of from 220° to 320° C.

10. The process of claim 7, wherein the catalyst is prepared by fluorinating $Al_2O_3$ with anhydrous HF.

11. The process of claim 10, wherein at least 90% of the alumina in said catalyst is fluorinated.

* * * * *